US005618502A

United States Patent [19]
Byers et al.

[11] Patent Number: 5,618,502
[45] Date of Patent: Apr. 8, 1997

[54] ZIRCONIUM AND HAFNIUM SEPARATION IN SULFATE SOLUTIONS USING CONTINUOUS ION EXCHANGE CHROMATOGRAPHY

[75] Inventors: Charles H. Byers, Knoxville; Warren G. Sisson; Thomas S. Snyder, both of Oak Ridge, all of Tenn.; Richard J. Beleski, Pittsburgh; Umesh P. Nayak, Murrysville, both of Pa.; Timothy L. Francis, Ogden, Utah

[73] Assignee: Westinghouse Electric Corporation, Pittsburgh, Pa.

[21] Appl. No.: 502,995

[22] Filed: Jul. 17, 1995

[51] Int. Cl.⁶ .......................... C01G 25/00; C01G 27/00
[52] U.S. Cl. .................................. 423/70; 423/73
[58] Field of Search .................... 423/70, 73, 79

[56] References Cited

U.S. PATENT DOCUMENTS

| 5,023,061 | 6/1991 | Snyder et al. | 423/70 |
| 5,024,749 | 6/1991 | Snyder et al. | 204/299 |
| 5,098,678 | 3/1992 | Lee et al. | 423/70 |
| 5,110,566 | 5/1992 | Snyder et al. | 423/70 |
| 5,112,493 | 5/1992 | Snyder et al. | 210/656 |
| 5,160,482 | 11/1992 | Ash et al. | 423/79 |
| 5,174,971 | 12/1992 | Snyder et al. | 423/70 |

OTHER PUBLICATIONS

G. L. Miller, "Zirconium", *Metallurgy Of The Rarer Metals*, Academic Press, Inc., New York, NY (1957), ch. 3, pp. 31–37, no month.
G. L. Miller, "Zirconium", *Metallurgy Of The Rarer Metals*, Butterworths Scientific Publications, London, England (1954), ch. 3, pp. 25–35, no month.

*Primary Examiner*—Steven Bos

[57] ABSTRACT

A method and system for improved continuous ion exchange chromatographic elemental separations of zirconium and hafnium and also for isotopic separations thereof from crude zirconium minerals by using zirconium (also containing hafnium) sulfate feedstock solutions, sulfate eluant solutions, anionic exchange resins, and reduced ion exchange column operating temperatures. The method and system of the invention provides sulfate feedstock solutions by completely converting the carbochlorination products of zircon sand to sulfate solutions prior to feeding to the ion exchange chromatographic column. The method and system of the invention is performed in a continuously operating continuous annular chromatograph (CAC). Nuclear grade substantially purified zirconium and hafnium metals are produced.

20 Claims, 4 Drawing Sheets

ZIRCONIUM AND HAFNIUM SEPARATION IN SULFATE SOLUTIONS USING CONTINUOUS ION EXCHANGE CHROMATOGRAPHY

1. FIELD OF THE INVENTION

The invention relates generally to the field of elemental separation processes and also to isotopic separation processes, and more particularly relates to methods and systems for continuously, partially or completely, separating and purifying zirconium (Zr) and hafnium (Hf) from crude zirconium minerals in order to provide nuclear grade zirconium metal and nuclear grade hafnium metal. The invention also relates to methods and systems for continuously, partially or completely, separating zirconium and hafnium isotopes from either crude zirconium minerals or from separated and purified solutions of zirconium and hafnium obtained from elemental separation processes in order to provide isotopically enriched nuclear grade zirconium metal and nuclear grade hafnium metal. Even more particularly, the invention relates to an improved zirconium and hafnium separation and purification method and system whereby zirconium and hafnium are separated and purified in a single operation using continuous ion exchange chromatography with sulfate feedstock solutions as the feed phase, sulfate eluant solutions as the mobile phase, and anionic exchange resins as the stationary phase.

The present invention concerns the chromatographic processing of zirconium to separate it from hafnium and to minimize its thermal neutron capture cross-section by altering its naturally occurring state thus enhancing its utility as a fuel rod cladding for nuclear reactors. It also concerns chromatographic processing of hafnium to separate it from zirconium and to maximize its thermal neutron capture cross-section by altering its naturally occurring state thus enhancing its utility as a nuclear reactor control rod material for nuclear reactors. The method and system of the invention accordingly improves the stability of zirconium and of hafnium as internal materials of construction for nuclear reactors.

2. BACKGROUND OF THE INVENTION

Zirconium metal has historically been used primarily as an internal material of construction for nuclear reactors, for instance, as claddings for uranium oxide nuclear fuel rods. Cladding of nuclear fuel rods, the primary end, provides an outer metallic jacket generally surrounding the nuclear fuel element which serves, inter alia., to prevent corrosion of the fissionable nuclear fuel and release of fission products into the coolant loop. Other attractive applications for zirconium metal are in the fabrication of corrosion-resistant chemical process hardware and advanced ceramics as oxides.

Particularly, materials for use in nuclear reactors are selected for their thermal neutron capture cross-sections, along with other properties. Zirconium is selected in nuclear application for, among other properties, its low, average thermal neutron capture cross-section (approx. 0.18 barns), good ductility, good resistance to radiation damage, and excellent corrosion resistance in pressurized hot water of temperatures up to about 350° C. The naturally occurring isotopic distribution of zirconium has a low average thermal neutron capture cross-section which is desirable for certain nuclear reactor materials. The naturally occurring isotopes of zirconium are given in Table 1.

TABLE 1

| Naturally Occurring Zirconium Isotopes | | |
|---|---|---|
| Isotope | Occurrence, % | Thermal Neutron Capture Cross-Section, Barns ($10^{-28}$ m$^2$) |
| $Zr^{90}$ | 51.45 | 0.03 |
| $Zr^{91}$ | 11.32 | 1.14 |
| $Zr^{92}$ | 17.49 | 0.21 |
| $Zr^{94}$ | 17.28 | 0.055 |
| $Zr^{96}$ | 2.76 | 0.020 |

However, there has been a continuing interest in reducing the tendency of nuclear grade zirconium to absorb thermal neutrons due to its contamination by neutron opaque hafnium. The more transparent the internal materials of construction of a nuclear reactor are to these thermal neutrons, the more efficiently the nuclear reactor will function since a certain number of these thermal neutrons are required to sustain the neutron triggered fission reactions. Accordingly, it is desirable to reduce the thermal neutron capture cross-section of the internal materials of construction of a nuclear reactor, such as zirconium.

Early efforts at reducing the thermal neutron capture cross-section of zirconium were directed to separating zirconium from hafnium, which by the way are the most difficult elements of the periodic table to separate. The two elements, zirconium and hafnium, occur together naturally, but hafnium has a substantially larger thermal neutron capture cross-section (almost 600 times that of zirconium). Thus the separation of zirconium from hafnium allows for the production of nuclear grade zirconium with a lower average thermal neutron capture cross-section by the elimination of hafnium.

Commercial processes currently available for the production of nuclear grade zirconium are variations of solvent extraction processes wherein zircon sand is converted to zirconium metal as a result of a somewhat involved series of steps. This extraction process requires the use of organic solvents, usually hexone, and various aqueous solutions, including hydrochloric acid. Hafnium, which is chemically similar to zirconium, must be separated from the zirconium. Usually a hexone/thiocyanate/hydrochloric acid system is employed for this purpose and requires a series of separate extraction steps along with separate separation columns. The zirconium, organic solvent and thiocyanate recovered from the hafnium separation steps are usually subject to additional processing to make sure that as much zirconium is recovered from the system as possible. The zirconium ultimately recovered from most extraction processes is in the form of pure zirconium oxide ($ZrO_2$). In the commonly used commercial process, the zirconium oxide is then chlorinated to form $ZrCl_4$, which is purified and subjected to Kroll reduction to produce zirconium metal suitable for nuclear applications. The aqueous and organic liquids used in the process typically include waste metals and other materials that must be properly discarded. One of the methods of treating these liquid wastes is to place them in holding ponds for future treatment and remediation. However, this is increasingly becoming an unacceptable waste management solution, particularly since federal and state laws relating to waste disposal have become more stringent.

These solvent extraction processes do effectively separate zirconium from hafnium in order to produce zirconium of the quality required for use in nuclear reactors and elsewhere in the nuclear industry. However, the increasing concern expressed by the public, the scientific community and the regulatory agencies regarding the waste generated by solvent extraction processes has lead the nuclear industry to explore alternative zirconium production methods which do not present the same waste management concerns.

Other zirconium and hafnium separation processes in addition to the aforementioned solvent extraction processes have been proposed. Recent efforts have proposed economically practical techniques of separation of zirconium from hafnium and also for separation of zirconium and hafnium isotopes therefrom by using continuous, steady-state, ion exchange chromatography in a continuous annular chromatograph (CAC) as taught in, for example, U.S. Pat. No. 5,023,061 (Snyder, et al.), U.S. Pat. No. 5,024,749 (Snyder, et al.), U.S. Pat. No. 5,098,676 (Lee, et al.), U.S. Pat. No. 5,110,566 (Snyder, et al.), U.S. Pat. No. 5,112,493 (Snyder, et al.), and U.S. Pat. No. 5,174,971 (Snyder, et al.). These patents all teach continuous methods and systems for simultaneously separating and purifying zirconium from hafnium and/or simultaneously isolating the fairly abundant low thermal neutron capture cross-section isotopes of zirconium and the high thermal neutron capture cross-section isotopes of hafnium in a single operation. While each of these teachings are technically feasible, optimization of the process for greater efficiency, lower waste generation and lower costs cannot be adduced therefrom. What is needed is a method and system for chromatographically separating zirconium from hafnium in a single operation using optimized processing parameters which provide for commercially important operations.

In the past, commercially acceptable zirconium and hafnium separations in a CAC device supported by using crude aqueous chloride feedstock solutions derived from the aqueous hydrolysis of the carbochlorination products of zircon sand, and by using aqueous chloride or sulfate eluant solutions along with cationic or anionic exchange resins have proved to be elusive. Zirconium product purity of less than 50 ppm [Hf]/[Zr], zirconium product concentrations of greater than 15 g/l [Zr], and product yields of about 90% have been unobtainable using crude aqueous chloride feedstock solutions in the CAC. What is need is an improved method and system for continuously separating and purifying zirconium and hafnium and also, if desired, for continuously and selectively enriching zirconium and hafnium isotopes, in order to produce nuclear grade materials by using continuously operating, steady-state, ion exchange chromatographic techniques and by using improved feedstock solutions and eluant solutions and improved operating conditions in a CAC device which provide substantially improved product purities, concentrations, and yields, while also eliminating both liquid waste discharge and organic reagents. Accordingly, the present invention addresses design improvements in order to improve the overall quality of the resultant nuclear grade materials in terms of: greater purification efficiencies, greater yields, simpler process design, lower operating costs, lower waste generation, and others.

3. SUMMARY OF THE INVENTION

It is an object of the invention to provide an improved continuously operating, steady-state, ion exchange chromatographic method and system for the separation and purification of crude zirconium minerals into zirconium and hafnium product fractions and/or into distinct isotope product fractions thereof, which results in improved purifies, concentrations, and yields of the nuclear grade zirconium and hafnium in the product fractions, while reducing waste generation and operating costs of prior methods and systems.

It is another object of the invention to provide an improved method and system for the separation and purification of zirconium from hafnium using continuous, steady-state, ion exchange chromatographic separation techniques based on sulfate solutions by using aqueous complexed zirconium (also containing hafnium) metal sulfate feedstock solutions as the feed phase and aqueous sulfate eluant solutions as the mobile phase and separating the materials on anionic exchange resins as the stationary phase.

In one aspect, the invention resides in a continuous method and system for separating and purifying zirconium and hafnium characterized by: (A) preparing a crude aqueous sulfate feedstock solution of zirconium and hafnium ions; (B) loading the sulfate feedstock solution to a continuous ion exchange chromatographic column containing an anionic exchange resin; (C) feeding an aqueous sulfate eluant solution to the column to elute the sulfate feedstock solution from the anionic exchange resin; and, (D) separately collecting at least one waste fraction, a substantially pure zirconium fraction, and a substantially pure hafnium fraction. The method and system can also further be characterized by: (E) separately processing the zirconium fraction and the hafnium fraction to produce nuclear quality zirconium and hafnium metal; (F) volume reducing the waste fractions for disposal; (G) recycling the eluant for reuse in step (C); and, (H) further recycling a mixed zirconium and hafnium fraction for reuse in step (B). The method and system of the invention can also further be characterized by: (I) separately processing the separated and purified zirconium fraction and hafnium fraction of step (D) to produce isotopically enriched nuclear quality zirconium and hafnium.

The method is preferably conducted in a steady-state, continuous manner, and it is particularly preferred to conduct it in a continuous annular chromatograph (CAC) instrument. The method can also be carried out at a reduced temperature of about 0° C. to 5° C. to additionally improve the Zr and Hf separations. It is preferred that the feed phase is an aqueous solution of anions based on a mixture of zirconium and hafnium in sulfate form. It is preferred that the mobile phase or eluant is an aqueous acid solution in sulfate form, preferably sUlfuric acid. It is preferred that the stationary phase is an anionic exchange resin.

In another aspect, the invention also resides in an improved method for preparing aqueous sulfate feedstock solutions of zirconium and hafnium ions from crude zirconium minerals which are used to support ion exchange chromatographic processing.

4. BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the spirit and scope of the appended claims. In the drawings, FIG. 1 is a graph of the elution order (idealized) of zirconium and hafnium chloride complexes on anionic exchange resin;

Figure 5:
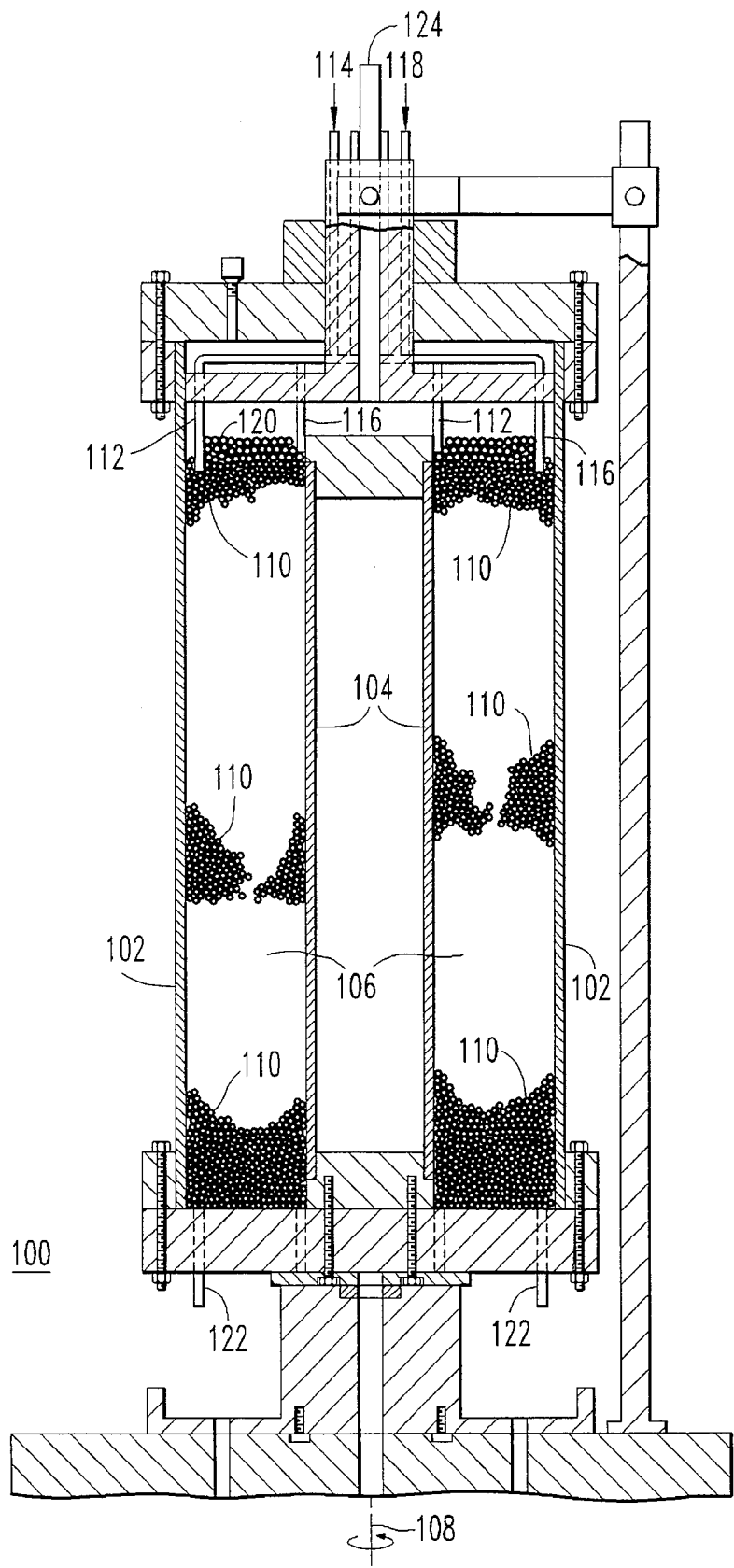
Figure 6:
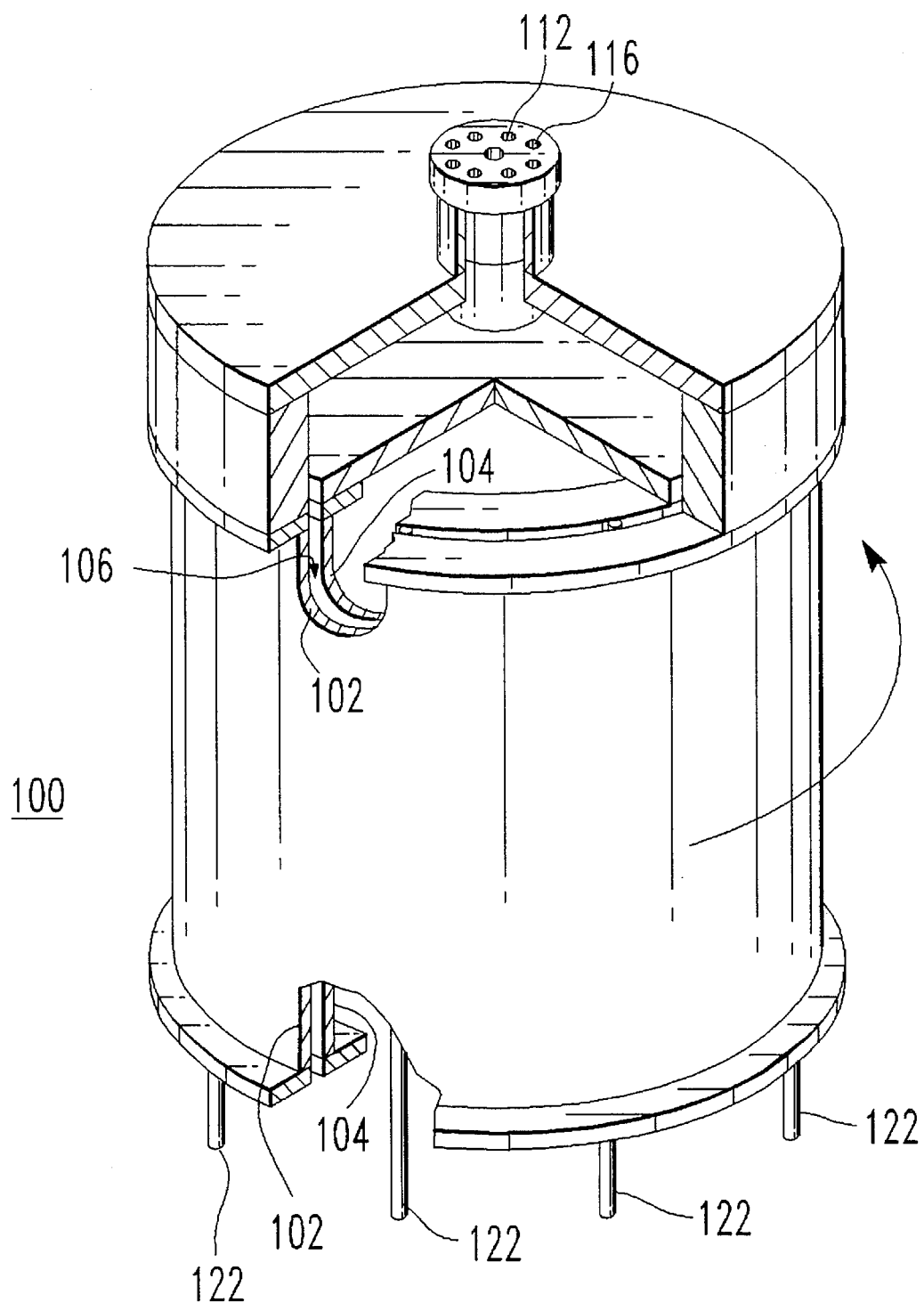

FIG. 5 is a side perspective view of a continuous annual chromatograph (CAC) with a portion in section to show the annular separation column suitable for use in the zirconium and hafnium separation method and system of the invention; and, FIG. 6 is a vertical sectional view of a continuous annular chromatograph (CAC) suitable for use in the zirconium and hafnium separation method and system of the invention.

5. DETAILED DESCRIPTION OF THE PREFERRED EMBODIMENTS OF THE INVENTION

The invention provides both the processing method and processing system for the continuous separation and purification of the elements zirconium (Zr) and hafnium (Hf) from crude zirconium minerals containing hafnium impurities in a single operation in a continuous annular chromatograph (CAC). The separated and purified zirconium and hafnium products can then be used as nuclear grade materials of construction for nuclear reactors. These products can also be used to support further separation processing in a continuous annular chromatograph (CAC), either concurrently in the same operation or subsequently in another operation, to isotopically enrich the separated and purified zirconium and hafnium products.

The :method and system of the present invention particularly improves the continuous, steady-state, ion exchange chromatographic separations of (1.) zirconium from hafnium and, if desired, (2.) zirconium and hafnium isotope enrichment in a continuous annular chromatograph (CAC) by using sulfate chemistry for the separations which results in improved product purities, concentrations, and yields, and also reduced waste, such that chromatographic processing can be done commercially as the means of separation of zirconium from hafnium.

The choice of sulfate-based systems offers advantages over chloride-based systems including, without limitation, higher metal solubility at higher concentrations of sulfate (e.g., $H_2SO_4$) eluant than in chloride (e.g., HCl) eluant, larger separation factors in sulfate systems (about 7) than in chloride systems (about 1.3), greater stability of the feedstock metal complexes of Zr and Hf in sulfate form, removal of metal impurities during feedstock preparation prior to separation, more rapid separation kinetics, reduced retention time in a CAC device, less corrosive effects of sulfates (e.g., $H_2SO_4$) over chlorides (e.g., HCl), etc.

In earlier efforts to improve zirconium from hafnium separations in a CAC device, the inventors focused on separations in pure chloride-based systems. This method comprised: (1) feeding to the CAC containing either cationic or anionic exchange resin an aqueous crude zirconium chloride feedstock solution of dissolved $ZrOCl_2$ (which also contained $HfOCl_2$) derived from the aqueous hydrolysis of a carbochlorination product of crude zircon sand; (2) feeding hydrochloric acid eluant solutions to the CAC; and, (3) recovering the separated and purified product fractions from the CAC. Co-pending U.S. patent application Ser. No. 08/502,944, of inventors C. H. Byers, W. G. Sisson, T. S. Snyder, R. J. Beleski, T. L. Francis, and U. P. Nayak, entitled *Zirconium and Hafnium Separation In Chloride Solutions Using Continuous Ion Exchange Chromatography*, teaches one optimized method of separating zirconium from hafnium in chloride solutions which avoids some of the pitfalls which have plagued these separations.

This above-identified co-pending patent application teaches that zirconium from hafnium separations in a CAC using pure chloride-based systems can be improved and nuclear grade materials can be produced in one instance by controlling the hydrolysis exotherm and also free acid generation typically associated with the preparation of conventional zirconium oxychloride ($ZrOCl_2$) feedstock solutions and also in the other instance by reducing the CAC operating temperatures. This, in turn, reduced the cross-polymerization of zirconium and hafnium which yield inseparable complexes of zirconium and hafnium. If formed, these inseparable complexes tend to impair the separation of zirconium from hafnium by contaminating the zirconium product wave front, which consequently diminished the overall quality of the resultant nuclear grade materials and also the yield. This cross-polymerization caused a reduction in the separability of zirconium and hafnium.

While cross-polymerization of zirconium and hafnium and inseparable zirconium and hafnium complex formation is effectively minimized in the chloride-based separation method of the aforementioned co-pending application and therefore provided a technically feasible operation, other economically related factors have caused the inventors to continue their search for a commercially effective separation method. One economically related factor includes the discovery that at high concentrations of the chloride eluant solution, the solubility of zirconium metal in the form of zirconium oxychloride complex is low (e.g., 200 g/l at 2N HCl, but 10 g/l at 6N HCl). This relationship causes the separation system to operate at more dilute than desirable HCl eluant concentrations which not only increases the metal retention time in the CAC column, but also increases the product recovery costs.

The inventors next attempted to use a mixed chloride-based and sulfate-based system for separations of zirconium from hafnium which was partially successful, however, zirconium product purity did not meet nuclear grade specifications of [Hf]/[Zr]<50 ppm and furthermore waste generation was increased as a result of generating mixed chloride and sulfate acidic solutions. This method comprised: (1) feeding to the CAC containing either cationic or anionic exchange resin an aqueous crude zirconium chloride feedstock solution of dissolved $ZrOCl_2$ (which also contained $HfOCl_2$) derived from the aqueous hydrolysis of a carbochlorination product of crude zircon sand; (2) feeding sulfuric acid eluant solutions to the CAC; and, (3) recovering the separated Zr and Hf product fractions from the CAC. This method relied on the interaction of the initial zirconium and hafnium chloride feedstock complexes and the sulfate eluant in the CAC column in order to directly convert the zirconium and hafnium chloride complexes to the sulfate form for chromatographic processing. Experiments indicated, however, that conversion of zirconium and hafnium chloride complexes to the sulfate form were not driven to completion in the chromatographic column of the CAC, leaving some remaining chloride complexes. This incomplete conversion caused a reduction in the separability of zirconium and hafnium.

The inventors unexpectedly discovered that the reduction in the separability of zirconium and hafnium and inability to achieve desired nuclear grade product purities was the result of two competing Zr and Hf elution wave fronts (with combined chloride and sulfate complexes) jockeying for position down the CAC column to determine which wave front elutes first. The result was zirconium having excessive product contamination with hafnium. While the zirconium sulfate wave front dominates the elution curve, sufficient hafnium chloride exits in the Zr product fraction to prohibit the zirconium product from meeting the nuclear grade specification. An idealized version of this competing wave front effect based on experimental results is shown in FIG. 1 and FIG. 2.

Figure 1:
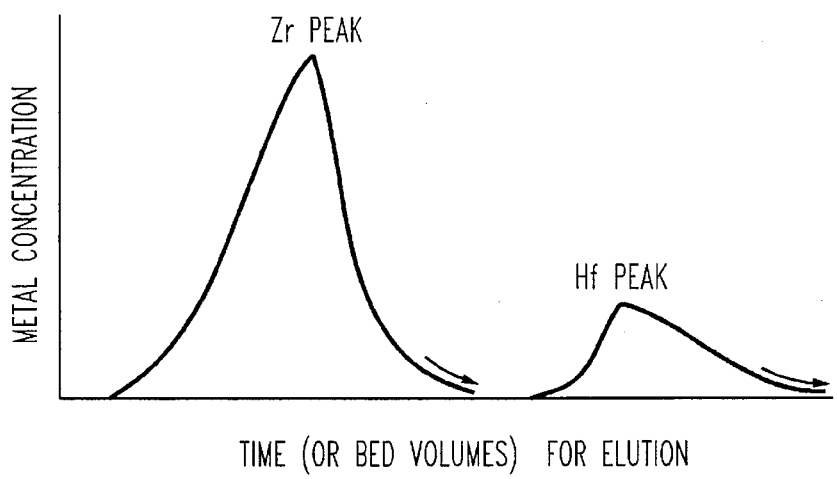
Figure 2:
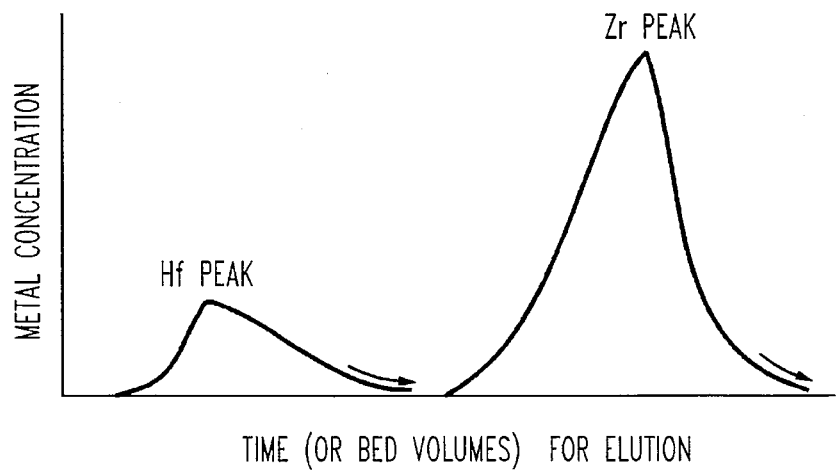
FIG. 2 is a graph of the elution order (idealized) of zirconium and hafnium sulfate complexes on anionic exchange resin.
Figure 3:
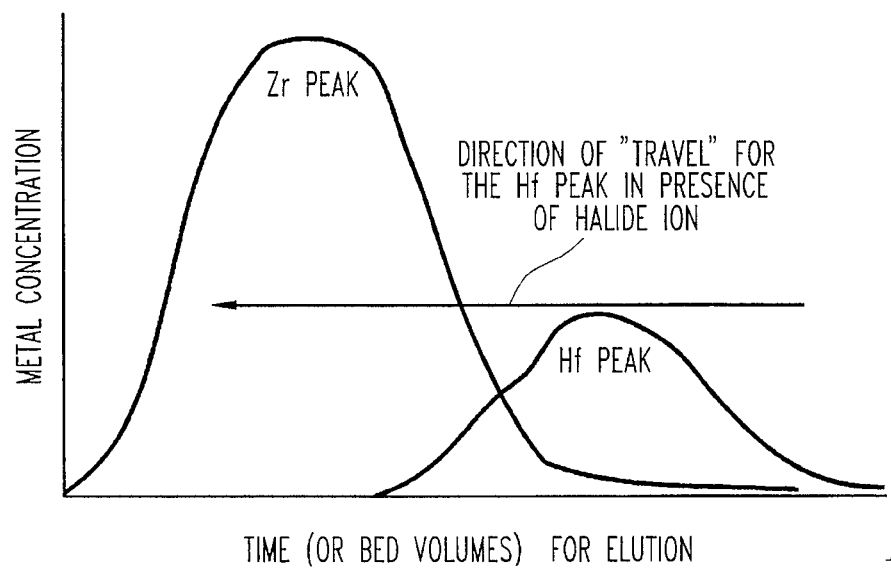
FIG. 3 is a graph of the impact (idealized) of chloride presence in sulfate-based systems on the elution order of zirconium and hafnium which prevents complete separation of zirconium from hafnium.

As shown in FIG. 1, on anionic exchange resins, eluting zirconium and hafnium chloride complexes with aqueous sulfuric acid solutions brings the hafnium wave front through the column first. While as shown in FIG. 2, on anionic exchange resins, eluting zirconium and hafnium sulfate complexes with aqueous sulfuric acid solutions brings the zirconium wave front through the column first. In the case of cationic exchange resins, the order of elution reverses uniformly for all species so that the incomplete conversion of chloride to sulfate problem remains the same. Therefore, the inventors have theorized that the trace metal chloride complexes remaining in the column due to incomplete conversion to sulfate draws the hafnium wave front "up" into the zirconium wave front, thereby preventing complete separation of Zr from Hf. FIG. 3 shows the impact of chloride presence on the Zr-Hf elution order in sulfate-based systems.

As a result the inventors were unable to provide a zirconium product purity to meet nuclear specifications of 50 ppm [Hf] in [Zr] using the mixed chloride-based and sulfate-based system. Additionally, the incomplete chloride to sulfate feedstock conversion process caused additional waste management problems, since the acid chlorides and acid sulfates produced in the metal recovery step must be further processed in order to separate the chlorides from the sulfates and recycle these materials or otherwise discard them. Further attempts were also made by the inventors to add trace amounts of hydrofluoric acid in the low parts-per-million to control complexing of the zirconium and hafnium during sulfate elution which was believed would improve separation in the mixed chloride and sulfate separation system. However, this approach was unsuccessful in improving separation because fluoride-based systems have the same elution order as chloride-based systems (i.e., halide elution systems). Again, the fluoride ion pulled the Hf wave front "up" into the Zr wave front, and the competing sulfate and fluoride wave fronts cancelled out the separation improvements.

The present invention overcomes the elution order issue in the mixed chloride-based and sulfate-based separation systems and its impact on product purity by completely converting zirconium and hafnium chloride complexes to sulfate complexes in the feedstock solution prior to injection to and separation in the CAC device, and also by using sulfate elution and anionic exchange resin. The present invention therefore provides a method and system for the production of nuclear grade zirconium and hafnium in sulfate solutions using continuous aqueous ion exchange chromatography which can be used commercially.

In the method and system of the invention, the feed phase can be any convenient aqueous feedstock solution of crude zirconium ions (which also contains hafnium ions) in soluble sulfate salt form. These crude zirconium sulfate feedstock solutions typically contain a natural distribution of zirconium isotopes and also hafnium impurities and it may also contain heavy metals and radioactive metals impurities derived from crude zirconium minerals such as zircon sand. However, the sulfate feedstock solutions can contain any partially refined mixture of zirconium and hafnium ions as well derived from a preliminary refinement process.

The mixed zirconium and hafnium sulfate complexes which are used as the aqueous feedstock solutions of the feed phase can be prepared either by: (1) chlorinating zircon sand and then converting the chlorination products to sulfate form; or (2) directly converting zircon sand to sulfate form through caustic or sulfate cracking of the zircon sand. While the inventors have identified these two methods to derive aqueous sulfate feedstock solutions of zirconium and hafnium ions to support chromatographic processing, the invention should not be considered limited to these methods since any method to provide an aqueous feedstock solution of zirconium and hafnium ions in soluble sulfate form can be used.

In a first method, the aqueous sulfate feedstock solutions can be obtained by the conversion of crude chlorination products of zircon sand ($ZrSiO_4$) to sulfate complexes. As in conventional chloride feedstock preparations, zircon sand (which typically contains a natural distribution of zirconium isotopes and also about 1 to 5% hafnium) is halogenated, for instance chlorinated, in the presence of a carbon source, such as coke, at temperatures of about 800° C. to 1100° C., typically about 1000° C., to yield a gaseous stream of a silicon tetrachloride ($SiCl_4$) fraction and a zirconium tetrachloride ($ZrCl_4$) (also containing $HfCl_4$) fraction, which fractions are further selectively separated in a differential condenser. An aqueous solution of hafnium and zirconium ions in soluble chloride salt form can then be prepared by dissolving and hydrolyzing the crude zirconium tetrachloride ($ZrCl_4$) (also containing $HfCl_4$) fraction in water or preferably in aqueous acid solution preferably sulfuric acid to obtain a solution of mixed oxychlorides of zirconium ($ZrOCl_2$) and hafnium ($HfOCl_2$). The aqueous mixed metal chloride solution is then converted to sulfate form by adding concentrated sulfuric acid solution to yield a 6 molar (M) or greater sulfuric acid concentration to insure precipitation of a sulfate product. The mixed metal sulfate precipitate is then isolated and redissolved in sulfuric acid to yield an aqueous sulfate feedstock solution of zirconium and hafnium ions. The aqueous crude sulfate feedstock solution can then be injected into the ion exchange chromatographic column of, for example, a CAC device containing anionic exchange resins and eluted with sulfuric acid solutions in order to separate and purify zirconium and hafnium in a single operation.

During this aqueous sulfate feedstock preparation method, it is desirable to control the exotherms and free acid generation during the aqueous hydrolysis reactions of the crude zirconium tetrachloride ($ZrCl_4$) (also containing $HfCl_4$) to yield an ionic solution of zirconium and hafnium complexed chloride solution. The hydrolysis exotherm has been discovered to produce cross-polymerized zirconium and hafnium complexes which are generally inseparable and are not amenable to ion exchange. Moreover, the free acids generated during the aqueous hydrolysis reactions accelerate and catalyze the formation of co-polymers of zirconium and hafnium. Therefore, the use of both two-stage hydrolysis and cooling to control both free acid generation and reactor temperature (both of which, if uncontrolled, enhance the cross-polymerization reactions) is desirable.

The inventors in their aforementioned co-pending U.S. patent application have invented certain methods used to control the hydrolysis exotherm and free acid generation and, accordingly, reduce the cross-polymerization of zirconium and hafnium during the feed preparations for chloride-based separation systems, which disclosure is incorporated by reference herein in its entirety. These methods are also effective in the subject invention to control the exotherm generated during the hydrolysis of zirconium tetrachloride ($ZrCl_4$/$HfCl_4$) prior to converting the hydrolysate to its sulfate form for use as a feedstock solution of complexed zirconium and hafnium sulfate which is used to support CAC separations of zirconium from hafnium according to the method and system of the invention. The hydrolysis of the crude chlorinated zirconium tetrachloride fraction (also containing hafnium tetrachloride) is therefore preferably performed under controlled conditions to substantially eliminate the formation of inseparable co-polymers of zirconium and hafnium.

The method used to control the hydrolysis exotherm and the amount of free acid generated from the hydrolysis reaction is to hydrolyze the zirconium tetrachloride fraction ($ZrCl_4$/$HfCl_4$) in a two-step partial hydrolysis process with cooling. In the first partial hydrolysis step, excess $ZrCl_4$/$HfCl_4$ is directed in the presence of water or aqueous acid to a hydrolyzer unit operated at controlled and reduced temperature of about 0° C. to 110° C., preferably about 10° C. to 25° C., by either using an external refrigeration jacket, injecting contact refrigerants, such as $CO_2$, $N_2$, or $O_2$, or by using other heat transfer means, to remove the heat generated during hydrolysis reaction. The lowering of the hydrolysis reaction temperature along with the continual removal of heat substantially eliminates the exotherm which is the driving force for cross-polymerization reactions. A partially hydrolyzed anhydrous crude zirconium oxychloride ($ZrOCl_2$) (also containing $HfOCl_2$) can be recovered. In the second step, the partially hydrolyzed crude $ZrOCl_2$/$HfOCl_2$ is dissolved in water or aqueous acid at a temperature of about 0° C. to 110° C., preferably about 10° C. to 25 ° C., to form aqueous metal complexed chloride solutions. Direct hydrolysis can also be used to control the exotherm by hydrolyzing the crude $ZrCl_4$/$HfCl_4$ in a hydrolyzer with crashed ice as the hydrolysis reagent and maintaining the temperature of the reaction solution at about 0° C. to 10° C. by external cooling.

Following this preparation to form zirconium and hafnium complexed chloride solutions, the next step is to convert substantially all of the zirconium and hafnium chloride complexes to sulfate form. Chloride solutions are precipitated out by sulfate solutions, e.g., 6M $H_2SO_4$ solutions or greater, with the resulting zirconium complexed sulfate, e.g., ($Zr(OSO_4)_2$/$Hf(OSO_4)_2$), or the like, being almost free of impurities aside from hafnium, of course. The sulfate form is advantageous over the chloride form since crude zirconium tetrachloride contains varying impurities of other metals in addition to hafnium. The making of the sulfate, however, results in a feed phase free of other metal impurities and allows the separation operation to be more consistent from run to run.

Other methods which can be used to form sulfate salts of Zr and Hf for the feed phase are by well known direct caustic or sulfate ore cracking methods for zircon sand. In this method, the zircon ore is made amenable to acid attack for example by heating to above 1000° C. and quenching before attacking with acid. Then sulfuric acid ($H_2SO_4$) is used to extract the zirconium in sulfate form by adding $H_2SO_4$ treatment to the pretreated ore and separating the silica by filtering the leach and then adding additional sulfuric acid, yielding iron-free sulfate which can redissolved and later precipitated as basic zirconium sulfate. These and other methods are well known in the art of extraction methods of zirconium from zircon.

It is preferred that the feed phase is an aqueous solution of zirconium (and also hafnium) anions in sulfate form. The uptake of zirconium and hafnium metals by anion exchange resins depends upon the formation of anionic complexes with Lewis bases such as $SO_4^{2-}$ from, e.g., $H_2SO_4$ or $Li_2SO_4$ as the complexing agent. Very strong anionic complexes, e.g., $Zr(OSO_4)_3^{2-}$, $Hf(OSO_4)_3^{2-}$ or other anions, are formed in sulfate solutions, even at low acid concentrations. This can be contrasted with chloride solutions in which at low acid concentrations, anionic complex formation, is negligible and, consequently, must be operated at very high acid concentrations to generate a zirconium based chloride anionic complexes which results in reduced solubility of the zirconium based chloride complexes. Practically, the solubility of the chlorides at concentrations where separation is effective is very low so that through put of a chloride-based separation is lower than practical.

Any zirconium and hafnium not convened to anionic form will not interact with the active group of the anionic resin stationary phase and not undergo separation. Unconverted zirconium and hafnium will most likely end up in the elution volumes with other impurities which do not interact with the stationary phase and will need to be reprocessed and recycled for separation. It is preferred to convert substantially all of the zirconium and hafnium present to anionic sulfate form. Zirconium crystallizes in 6M $H_2SO_4$ forming a precipitate of $Zr(OSO_4)_2.4H_2O$ and, therefore, 6M $H_2SO_4$ is the upper limit of acid concentration which can be used to form the anionic complexes for the feed phase. It is preferred to use an acid concentration in the feed phase for anionic complex formation of about 2 to 4M $H_2SO_4$ with 6M $H_2SO_4$ as the upper limit. It is most preferred to form anionic complexes in about 2M $H_2SO_4$ as the feed phase.

It is preferred that the feed phase have a concentration of zirconium as is compatible with the solubility under anticipated operating conditions, that is, the feed phase should be as concentrated as possible without exceeding the solubility limit for the solute. The natural consequence of chromatographic separation is a dilution of the concentration of products being separated into product streams. Therefore, the overall efficiency of the process and particularly a minimization of the efforts needed to recover the desired products from the product streams is better served by using as high a concentration as possible without creating an undue risk that zirconium and hafnium will precipitate out during the course of the process.

It is preferred to use a zirconium concentration in the feed phase of about 50–200 g/l, most preferably about 100 g/l Zr in 2M $H_2SO_4$. At 25° C., the solubility of zirconium in 2M $H_2SO_4$ is estimated to be about 100 g/l.

The mobile phase may be an aqueous acid solution capable of selectively solvating the zirconium and hafnium ions such that they can be eluted down the column. The mobile phase or eluant is an aqueous fluid capable of displacing the zirconium and hafnium ions from their ionic association with the stationary phase. The mobile phase preferably has an acid strength somewhat lower than that of the feed phase and it is preferred to use an acid concentration in which zirconium has a greater affinity for the stationary phase than hafnium. The eluant can be $H_2SO_4$, HCl and water. However since the sulfate is most compatible with the feed phase in sulfate form, use of $H_2SO_4$ as the eluant simplifies eluant recycling. If not, mixed $Cl^-$/$SO_4^{2-}$ acid solutions in eluant would have to be segregated prior to recycling of the liquid reagents. Moreover, any complexing of the metals with chloride will result in reduced separability of zirconium and hafnium, such that the preference is to use sulfuric acid as the eluant. Preferably, the mobile phase has an acid concentration of about 1 to 4M $H_2SO_4$, preferably about 1 to 2M $H_2SO_4$. The precise acid strength needed will depend upon the nature of the active groups of stationary phase and the eluant acid. It is also possible to use water as the eluant since it will form a more dilute solution of the feed phase acid as it passes down the column.

It is most preferred that the eluant have a lower acid concentration when eluting hafnium which exits the column first on anionic resin stationary phase and then step up the acid concentration of the eluant to elute zirconium which exits the column second. Zirconium anionic complexes are more strongly held on the anionic exchange resin stationary phase than hafnium complexes. Therefore, as soon as hafnium is removed from the column, a more strongly held zirconium can be concentrated on the column by stepped up elution with a second eluant at a higher concentration than the primary eluant used to elute hafnium. Removal of the hafnium fraction in the first product wave front facilitates the use of step elution to concentrate the zirconium product fraction and also remove zirconium quickly. This is one of the advantageous features of using anionic exchange separation of hafnium and zirconium sulfate anionic complexes by continuous ion exchange chromatography, since step elution, which can only work for the last wave front in gradient elution, can be used to remove zirconium as soon as hafnium exits which can result in a much quicker elution and a higher concentration of zirconium exiting the CAC column.

It is preferred to first elute Hf with a primary eluant acid concentration of about 1 to 2M $H_2SO_4$, and after Hf emerges, increase the concentration of the eluant to about 3 to 4M $H_2SO_4$, while always being below the acid concentration at which Zr will precipitate out of solution.

The stationary phase can be any anionic exchange resin having an affinity for zirconium anions in soluble sulfate salt form, typically in aqueous solution as $Zr(OSO_4)_3^{2-}$ or the like. It is preferred that the anionic exchange resin display a very strong affinity for zirconium anions in the feed phase as reflected by a large solid to liquid distribution coefficient. It is also preferred that the anionic exchange resins have the highest ionic capacities per unit volume as possible, typically in excess of 0.5 milliequivalents per milliliter. It is also preferred that the stationary phase have a monodisperse distribution of particles, preferably in the form of spherical beads. An average particle size of 0.1 to 100 microns is preferred, most preferably about 25 to 100 microns. A particle size of 10 microns or less in order to maximize the surface to volume ratio is ideal for separation efficiency, since the exchange reaction occurs at the surface of the resin beads of the stationary phase. But smaller sizes can pose problems of insufficient permeability for economically desirably flow rates and also problems of how to retain the resin beads in the column.

The resin beads are preferably divinyl benzene crosslinked styrene copolymers. Particularly preferred active groups of anionic exchange resins are those based on ammonium groups derived from primary and tertiary amino groups (weakly basic) and the quaternary ammonium groups (strongly basic). Preferred anionic exchange resins are Dowex 1 with an active group on the polystyrene based resin matrix of $R-CH_2N^+(CH_3)_3$ (trimethyl alkyl or benzyl ammonium Type I resins) and Dowex 2 with an active group on the polystyrene-based resin matrix of $R-CH_2N^+(CH_3)_2 C_2H_4OH$ (dimethylhydroxy alkyl ammonium Type II resins), both resins manufactured by Dow Chemical Corporation and both being strongly basic anionic exchange resins.

Dowex 1 resins with 2–12% crosslinking between the copolymer backbone of styrene and divnyl benzene is preferred, while Dowex 1 resins at either 2–8% crosslinking are being especially preferred, with 4% crosslinking being most preferred. Other anionic exchange resins which can be used as the stationary place include the Amberlite IRA series of anionic exchange resins from Rohm and Haas Company. Reference can be made to Perry's Chemical Engineers Handbook, 6th edition (1984), pp. 16–1 to 16–48 including Table 16–4 for a description of other anionic exchange resins suitable for use in the method and system of the invention.

The anionic exchange resin further provides an effective method to separate from the feed phase the contaminant metals, since these metals are not held up in the exchange reaction in the column stationary phase and predominately exist in cationic form which can be recovered separately from the column. Moreover, in the method of the invention, the sulfate feedstock preparation method substantially eliminates the contaminant metal impurities prior to feeding to the separation column which advantageously results in reduced waste generation.

It is preferred to have a product concentration of [Zr] greater than about 10 g/l, preferably greater than about 15 g/l, most preferably greater than about 25 g/l with gradient elution and [Hf] greater than about 0.5 g/l. It is further preferred to attain a product purity of less than 50 ppm [Hf] in [Zr], preferably less than 20 ppm [Hf] in [Zr]. It is further preferred to operate at a yield of about greater than 50%, preferably about greater than 90%, and most preferably about 95–98%.

Figure 4:
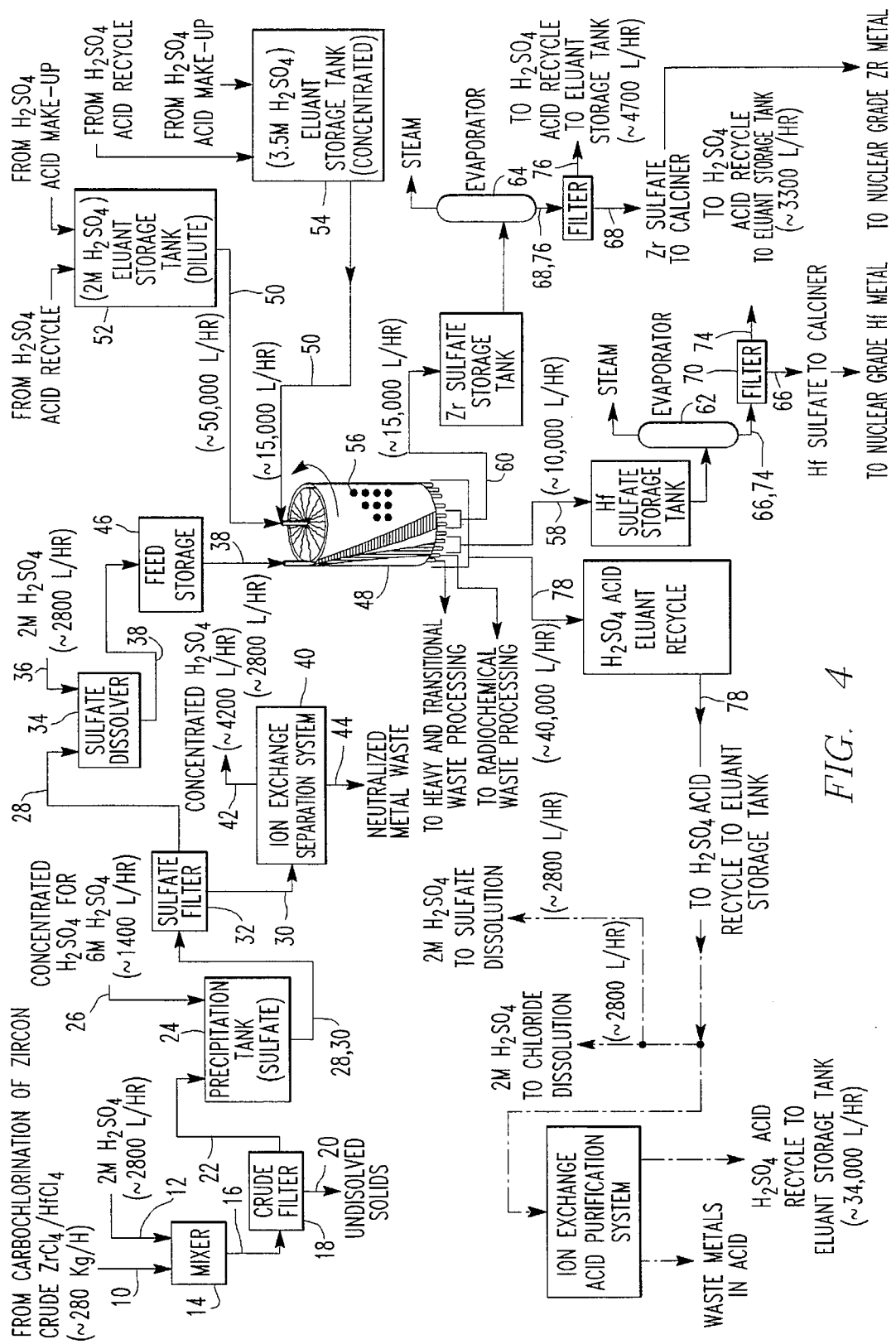
FIG. 4 is a schematic flow diagram of the zirconium and hafnium separation method and system of the invention.

Referring now to the drawings, FIG. 4 shows a schematic of a commercial method system for separating zirconium from hafnium in sulfate solutions using continuous ion exchange chromatography. As shown in FIG. 4, a crude $ZrCl_4/HfCl_4$ fraction (10), previously derived from the carbochlorination of zircon sand, is mixed with dilute sulfuric acid solution (12), preferably about 2M $H_2SO_4$, in a mixer (14) to dissolve the crude $ZrCl_4/HfCl_4$ fraction to yield an aqueous chloride solution of zirconium and hafnium (16). The dissolution of the $ZrCl_4/HfCl_4$ fraction is preferably carried out by the aforementioned two-step hydrolysis technique with cooling for control of the hydrolysis exotherm and cross-polymerization reactions. The hydrolysate solution (16) is then filtered in a filtration tank (18) to remove any undissolved solids (20), mainly undissolved silica from the zircon sand and other impurities.

The filtered chloride solution (22) is then fed to a precipitation tank (24) along with concentrated sulfuric acid (26) and the acid concentration is increased to at least 6M $H_2SO_4$. The zirconium complexed chloride solution (22) is precipitated out as zirconium complexed sulfate (28) and supernatant (30). The zirconium complexed sulfate precipitate (28) is then filtered in a filter (32) and separated from the supernatant (30) of concentrated $H_2SO_4$ and also including other impurities, e.g., Fe, Al, P, Si, etc. The filtered sulfate precipitate (28) is then directed to a dissolution tank (34) with dilute sulfuric acid (36), preferably 2M $H_2SO_4$, to yield an aqueous sulfate feedstock solution (38) of zirconium and hafnium ions. The filtered supernatant (30) can optionally be further processed in an ion exchanger (40) in order to separate the concentrated $H_2SO_4$ (42) for reuse from the metal wastes (44). The aqueous sulfate feedstock solution (38) is then directed to a feedstock storage tank (46).

The sulfate feedstock solution (38) is then fed to a continuously operating ion exchange chromatographic column (48), preferably a continuous annular chromatograph (CAC) device, along with a sulfate eluant solution (50). Preferably the sulfate eluant solution (50) is derived first from an eluant storage tank (52) containing a dilute sulfate eluant, preferably about 2M $H_2SO_4$ eluant for Hf elution, and then is derived from a second eluant storage tank (54) containing a more concentrated sulfate eluant, preferably about a 3.5M $H_2SO_4$ eluant for Zr elution. The CAC column (48) is preferably filled with anionic exchange resin beads (56), which fills the ion exchange column but is shown as only partially filling the column for ease of illustration.

A purified hafnium product fraction (58) in soluble sulfate salt form is removed from the CAC (48) and a purified zirconium product fraction (60) in soluble sulfate salt form is removed from the CAC (48). Also waste product fractions (not shown) which comprise radiochemical wastes and/or heavy and transitional metal wastes are removed from the CAC column as separate product fractions and subsequently volume reduced for disposal. The two products (58) and (60) are then fed to evaporative crystallizers (62) and (64), respectively, and concentrated hafnium (66) and zirconium (68) products are recovered as sulfate salts in filters (70) and (72), respectively, while concentrated sulfuric acid (74) and (76) is recycled. Alternatively, a membrane separation process such as reverse osmosis followed by precipitation process can be employed to concentrate the hafnium and zirconium fractions. The Hf sulfate (66) and Zr sulfate (68) fractions are then directed to a calciner (not shown) or spray roaster (not shown) for recovery as substantially pure zirconium oxide ($ZrO_2$) and hafnium oxide ($HfO_2$), and then subsequently reduced (not shown) such as by Kroll or hydrogen reduction to nuclear grade zirconium metal and nuclear grade hafnium metal. The eluant recycle (78) from the CAC can further be processed and purified by ion exchange prior to recycling. The aqueous zirconium sulfate product fraction (58) and hafnium sulfate product fraction (60) prior to the product recovery steps can be further separated into isotopes thereof by chromatographically processing these solutions separately in another CAC device (not shown).

The effective ion exchange chromatographic column height should be sufficient to allow significant resolution of the hafnium and zirconium into distinct product fractions. If desired, the effective column height may be increased to allow significant resolution of various isotopes of the element of interest, zirconium or hafnium, into distinct product fractions. The resolution is preferably sufficient to yield an element or isotope purity of at least about 50%, preferably in excess of about 90%, more preferably at least about 98%. It is preferred that this resolution be effected in a single pass through the column. The effective column height needed for a given resolution can be estimated from an application of the Kremser-Brown-Saunders equation, to empirical data on the separation capacity of a feedstock, ion exchange resin, eluant, and flow conditions.

A theoretical separation factor, $\alpha_t$, is used to define the ability to separate the various elements or isotopes. This factor $\alpha_t$ is itself defined by the following formula for the binary case:

$$\alpha_t = (y/(1-y))/(x/(1-x)),$$

where y is the molar concentration of the desired element or isotope in a product rich fraction ("heads") in that element or isotope, and x is a molar concentration of the same element or isotope in the product poor fraction ("tails") in that element or isotope. Actual stage separation factors, $\alpha_s$, are conveniently evaluated on 25 to 100 centimeter test columns, which a 25 centimeter column being preferred. The preferred feedstocks, eluants, ion exchange resins and flow conditions should yield a separation factor of about 1.001 to 1.15, preferably about 1.03 to 1.10. The effective column length for the desired separation is then determined by estimating the number theoretical stages, N, required of 25 centimeter each in length by the following formula:

$$N = \ln \alpha_t / \ln \alpha_s,$$

where N is the number of stages per 25 cm column.

The effective column height can be vertical, but it can also have other orientations. What is important is the effective path over which the mobile phase travels. It is preferred that the path be provided in such a way that the chromatographic separation can be operated continuously. Presently, there is no convenient technique available for instantaneously sensing the concentrations of the product fractions. Thus, there is a preference for a continuously operating method which has reached steady-state, so that a particular product fraction reproducibly has a certain product distribution. If the ion exchange chromatographic separation is effected in a discontinuous or batch manner, random variations between runs may make it difficult to reproducibly collect product fractions with the same product distribution from run to run. For instance, if a single vertical column is loaded in a batch manner the elution time of the product fraction rich in a particular product may vary from run to run due to random variables difficult to control such as feedstock concentration fluctuations, etc.

It is further preferred according to the method and system of the invention to optimize the separation kinetics through control of column temperature during ion exchange chromatographic operations. Zirconium and hafnium separation kinetics have been shown to be temperature dependant with the maximum separation factor obtained between about 0° C. and 5° C. Thus, by controlling the column temperature and also the temperature of the feedstock and eluant solutions, the present invention tends to optimize the separation of zirconium from hafnium.

The structure of the continuous annular chromatograph (CAC) (48) as shown in FIG. 4 suitable for use in the method and system of the present invention is shown in FIGS. 5 and 6. A detailed description of the materials of construction, design and operation of a CAC can be found in the earlier mentioned U.S. Patents, which are incorporated by reference herein in their entireties. A particularly preferred continuously operating chromatograph is a CAC developed by Oak Ridge National Laboratory. As shown in FIGS. 5 and 6, the CAC device (100) comprises two concentric cylinders (102) and (104) which define an annular column (106) which can be rotated about the axis (108) of the annular column. The annular column (106) includes a stationary phase material (110), such as anionic exchange resin beads, packed between the two concentric cylinders of differing diameters with vertical axes to form the annular column. For ease of illustration, the anionic exchange resin beads (110) are shown as only partially filling the annular column.

One or more feedstock ports (112) are provided at a given angular position with supplies a crude zirconium/hafnium complexed sulfate feedstock solution (114) to the ion exchange resin beads (110) packed in the annular column (106). One or more eluant ports (116) are provided at some angular offset position from a feedstock port(s) which supplies a sulfate eluant (118) to a layer of glass beads (120) which sit atop the resin beads (110). It is preferred to place a layer of glass beads (120) above the stationary phase material, and to feed the eluant (118) on the top of the glass beads while feeding the crude zirconium/hafnium sulfate feedstock (114) directly to the top of the stationary phase (110) to prevent any undesired mixing effects.

The CAC device (100) also includes a number of product delivery ports (122) set at different angular positions which can be set arbitrarily to accommodate particular operating conditions. Each product port (122) collects an elution volume containing a distinct product fraction which has a particular residence time in the CAC. The CAC is operated by rotating the annular column packed with ion exchange resin beads by a motor (not shown) at a constant speed so that any vertical segment of the annular bed is above a particular fixed product collection port at a given time after this segment has been loaded with crude zirconium/hafnium sulfate feedstock and eluant. Thus, each product collection port has an angular position which corresponds to a particular elution time for a particular rate of rotation of the stationary phase and for a particular flow rate through the stationary phase.

The flow rate through the stationary phase is controlled by the pressure drop across the effective height of the stationary phase and the physical characteristics of the stationary phase, i.e., particle size and packing void volume. This pressure drop may be provided by the hydrostatic head of the feedstock and eluant, but it is preferably provided by pressurizing the CAC device at pressure valve (124). The pressure required to achieve a particular flow rate is governed by the nature of the stationary phase. The smaller the average particle size of the resin beads making up the stationary phase, the larger the pressure drop required to obtain a particular flow rate over a particular effective height will be. However, the separation factor for any given theoretical stage is improved as the average particle size of the resin beads is decreased. Thus, the effective height needed to effect a given degree of separation is decreased as the separation capacity of a unit length (or theoretical stage height) is increased by decreasing the average particle size of the resin beads.

A short residence time in the chromatograph allows an increase in the zirconium and hafnium concentration in the product elution volumes. In general, the longer the residence time in the chromatograph is, the more "band spreading" occurs. "Band spreading" is a term of art used in this context to describe the phenomenon that can be observed when the longer the residence time is, the larger the proportion of the total elution volume which contains some of the desired product. To obtain all or a certain percentage of this product fraction, it is necessary to collect a volume of eluant which increases with residence time. Thus, the net effect of band spreading is to dilute the metal concentration in the product fractions.

The flow rate across the effective height of the stationary phase and the rotational speed of the stationary phase should be coordinated so that a particular product fraction always elutes at the same angular position and, consequently, is always delivered to the same product collection port.

It is preferred that the chromatograph be operated in a displacement mode wherein no more than about 5 percent, more preferably no more than about 1 percent of the effective column height, is loaded with feed solution before elution is initiated. The angular displacement between the feed port and the eluant port and the speed of rotation of the annular bed are coordinated so that the time interval between loading and elution is just sufficient for the desired degree of penetration. The relationship between the time for loading and the depth of penetration is in turn governed by the flow rate through the annular bed.

The displacement may be effected by either an isocratic or a gradient supply of eluant. In the former case, the eluant can simply be supplied from a single port while in the latter case, several ports at successively greater angular displacements from the feed port are utilized. In the gradient mode, elution under the influence of the initial eluant is permitted to proceed until some separation has been effected, and then eluant with a higher concentration is supplied. This increases the migration speed down the column and minimizes the range of elution volumes or times over which a given component or product fraction will exit the column or, in other words, this procedure minimizes the band spreading.

Decreasing the elution volumes by gradient elution or by other means increases the concentration of the product in the product fraction. Concentrations greater than about 2 g/l, preferably greater than about 15 g/l, especially between about 20 and 70 g/l are preferred. It is preferred to maximize the concentration of product because the total volume of fluid to be processed will be reduced. This allows a reduction in the overall size of the system with a consequent reduction in capital and operating expenses. However, practical considerations, such as solubility limits, will constrain the maximum concentrations obtainable. In the method and system of the invention, gradient elution is initiated for the zirconium wave front after the hafnium wave front has emerged from the column.

The flow rate down the chromatograph is governed by the pressure drop from the top to the bottom of the chromatograph and the nature of the stationary phase. The smaller the average particle size of the resin beads making up the stationary phase is, the higher the pressure drop that is required to obtain a given flow rate. This relationship is also affected by the particle size distribution of these resin beads. There is, however, a maximum attainable flow rate for any given resin stationary phase which cannot be exceeded by the application of additional pressure. The suppliers of such resins rate them in terms of flow rate per given pressure drop and maximum attainable flow rate.

It is preferred to use a stationary phase which will permit flow rates between about 2 and 80, more preferably between about 3 and 20 gallons per minute per square foot of cross-sectional area (between about $1.36 \times 10^{-3}$ and $5.43 \times 10^{-2}$ m³/sec, more preferably between about $2.04 \times 10^{-3}$ and $1.36 \times 10^{-2}$ m³/sec per square meter of cross-sectional area). There is a relationship between the achievable flow rates and the effective chromatograph column height needed for a given degree of purity. For a given system of stationary phase and eluant, the theoretical stage separation factor, $\alpha_s$, of the stationary phase will increase as the average particle size of the resin beads of the stationary phase decreases. However, as this particle size decreases, so does the flow capacity of the stationary phase. Thus, there is an inverse relationship between $\alpha_s$ and the flow capacity. A higher flow rate will require a greater effective column height to achieve the same degree of separation or product fraction purity.

Furthermore, there is the additional constraint that the pressure required to achieve the desired flow rate should not exceed the capability of available pumps, seals and feed tubing. The required pressure is a function of both the pressure drop needed per unit of effective height and the total effective height required for the desired degree of separation. Thus, as the flow capacity of the stationary phase is increased by a change in its physical configuration and, consequently, its theoretical stage separation factor, $\alpha_s$, is decreased, the required effective height and the required overall pressure drop are both increased. On the other hand, as the theoretical stage separation factor, $\alpha_s$, is increased by a change in the resin bead size distribution so that the flow capacity of the stationary phase is decreased, the pressure drop for a given effective height is increased. A preferred pressure drop of less than about 2759 kPa (400 psi), more especially between about 345 and 1042 kPa (50 and 150 psi), is preferred.

Thus, to obtain a system with a commercially practical capacity, it is necessary to use a stationary phase which will simultaneously display both a reasonable theoretical stage factor, $\alpha_s$, and a reasonable flow rate per unit of effective height with a reasonable pressure drop. This can be achieved by an appropriate selection of both the capacity of the stationary phase resin and eluant.

It is preferred that several product collection ports be used to collect a particular product fraction. This is accomplished by closely spacing these collection ports so that they more than span the angular range of rotation that corresponds to the elution time interval of that particular fraction, but do not extend to angular positions at which any significant portion of any other product fraction is expected to elute. Of course, this requires that the elution time intervals of different product fractions do not substantially overlap. That is, the alpha ($\alpha_s$) values should exceed 1, and should preferably be in the range of about 1.03 to 1.1, for all species. This arrangement tends to insure that minor fluctuations in the steady-state elution behavior which would cause a slight advancement or retardation of the elution time of the desired product fraction will not result in any loss of this fraction.

As the chromatograph rotates continuously, the product fractions in the feed are separated so that they are angularly displaced from the feed inlet. The four product fractions of primary concern are the zirconium fraction, the hafnium fraction, the heavy and transition metal waste fraction, and the radiochemical waste fraction. An additional product fraction also represents any miscellaneous product present in the feed solution which can be recycled to the column for further processing. The separated product fractions are collected in the collection vessels and processed further for recovery of zirconium and hafnium metals.

Only a single continuous annular chromatograph has been described in connection with the present process. However, any number of continuous annular chromatographs may be employed in the present process. For example, two or three such chromatographs may be effectively used. Each chromatograph unit would require a supply of zirconium/hafnium sulfate feed and would produce the product fractions described above.

Table 2 below sets forth the chromatographic operating conditions preferred for achieving the efficient and effective separation and purification of zirconium and hafnium in accordance with the method and system of the present invention.

TABLE 2

Preferred Ion Exchange Chromatographic Operating Conditions

| | Range | Preferred |
|---|---|---|
| Feedstock Phase (Zr and Hf Ions in Sulfate Solution) | | |
| Concentration | 0 to 3M | 0 to 2M |
| Solvant | | |
| Water | Water | |
| Anions | $H_2SO_4$ | |
| Acid Concentration | 0 to 3M | 0 to 2M |

TABLE 2-continued

Preferred Ion Exchange Chromatographic Operating Conditions

| | Range | Preferred |
|---|---|---|
| Stationary Phase (Anion Exchange Resin) | | |
| Particle Size Mean Distribution | Strong Base or Weak Base Anionic Exchange Resin | Dowex 1 and 2 |
| | 01 to 500 microns | <100 microns |
| | Polydisperse to Monodisperse | Monodisperse |
| | Arbitrary | Spherical |
| Mobile Phase (Eluant) | | |
| Solvent | Water $H_2SO_4$ | $H_2SO_4$ |
| Acid Concentration | 0 to 6M | 0 to 2M for HF Elution 0 to 2M for Zr Elution |
| Elution Mode | Gradient and Isocratic | Gradient |
| Temperature | 0° C. to 25° C. | 0° C. to 5° C. |

The following Example is provided to illustrate the preparation of sulfate feedstock solutions of zirconium and hafnium ions through conversion of substantially all of the zirconium and hafnium metal species in chloride form to sulfate form and removal of the free chloride ions therefrom. The Example is intended to be purely exemplary. Other variations of the invention will be apparent from a consideration of the specification or from the practice of the invention.

EXAMPLE 1

Preparation of Sulfate Feedstock Solutions of Zirconium and Hafnium Ions for Ion Exchange Chromatographic Processing in a Continuous Annular Chromatograph (CAC)

1. A crude $ZrCl_4$ (also containing $HfCl_4$) powder containing all of the natural impurities is dissolved slowly in about 2M $H_2SO_4$ at about 5° C., in a chilling bath, so that the temperature excursion during dissolution is no more than about 2° C. A 100 g/l Zr solution is the standard mixture. The supernatant solution yields an intense yellow color and also contains trace undissolved material. The solution is then refrigerated. The solution can optionally be filtered to remove the insoluble impurities from the solution. A slow addition of the crude $ZrCl_4$ to about 2M $H_2SO_4$ is preferred to eliminate spattering caused by the release of HCl gas. Furthermore, good ventilation is preferred again because of the evolution of HCl gas.

2. After steady-state acid dissolution is achieved, the dissolved chloride is optionally filtered on filter paper resulting in a crystal clear solution with varying amounts of solid impurities left behind on the filter paper.

3. Concentrated sulfuric acid ($H_2SO_4$) is mixed at from about 5° C. to room temperature (approx. 30° C.) with the Zr solution (about 1 volume acid to 2 volumes Zr solution resulting in an over 6M $H_2SO_4$ solution) which results in precipitation of a white zirconium and hafnium sulfate powder from the solution. Zirconium and hafnium ionic species are virtually insoluble in 6M $H_2SO_4$ and so the concentration to which the sulfuric acid is brought up to insures precipitation of the sulfate product. Because of the dilution of the $H_2SO_4$ solution, the mixture is cooled as the concentrated acid is added. Clearly the disposal of the 6M $H_2SO_4$ solution which contains chloride, iron, and other metal impurities is a waste management concern which should be addressed.

4. The crystal magma are then placed in a fretted glass filter (M or C) and vacuum filtered. The solid crystal becomes a porous cake and a bright yellow liquid passes through the filter, presumably containing iron and other metal impurities typically present in crude $ZrCl_4$ but now removed, to make a uniform starting sulfate feedstock for separation with consistent results.

5. The filter cake is then washed at least once, preferably twice, with a solution of 62.5 cc water, 33.3 cc concentrated $H_2SO_4$, and 3.2 cc conc. HCl per 100 cc of total solution. Some yellow remained on the solid before the second wash, but afterwards the solid was completely white. This solution can be replaced by 6M $H_2SO_4$. However, the HCl bearing wash solution was used to remove chloride, but in the industrial process, it is desirable to use as little HCl as possible and add not HCl to the solution.

6. The solid crystals are then washed with acetone and allowed to dry to produce relatively purified crystals as evidenced from chromagraphs showing no stray peaks. Obviously the acetone drying will be omitted from the industrial approach since wet powder will be dissolved in 2M $H_2SO_4$ and this solution will provide the sulfate feedstock.

7. Now the zirconium and hafnium metal complexes in soluble sulfate salt form are dissolved to the starting volume in the original $ZrCl_4$ solution using 2M $H_2SO_4$ as the solvent. The resultant Zr sulfate solution should be approximately 100 g/l Zr solution, which is within a few g/l of saturation at room temperature. Dissolution is easily achieved with no heating evident and the solution is clear indicating no presence of chloride, iron or other metal impurities. This solution can now be used as the aqueous zirconium and hafnium sulfate feedstock solution or feed phase for injecting into the CAC.

Industrial Applicability

The process of the present invention will find its primary application in the production of nuclear quality zirconium and hafnium metals and, if desired, isotopically enriched zirconium and hafnium metals for nuclear reactor construction materials when it is desired to employ a simple, low cost process for the separation and purification of zirconium and hafnium and isotopes thereof.

The invention having been disclosed in connection with the foregoing variations and examples, additional variations will now be apparent to persons skilled in the art. The invention is not intended to be limited to the variations specifically mentioned, and accordingly reference should be made to the appended claims to assess the spirit and scope of the invention in which exclusive rights are claimed.

We claim:

1. A continuous method for separating and purifying zirconium from hafnium, which comprises:

(a) preparing an aqueous sulfate feedstock solution of zirconium and hafnium sulfate complexes;

(b) loading said aqueous sulfate feedstock solution to a continuously operating chromatographic ion exchange column containing anionic exchange resin;

(c) feeding an aqueous sulfate eluant solution to said column to elute said aqueous sulfate feedstock solution from the anionic exchange resin; and, (d) separately collecting a substantially pure zirconium fraction and a substantially pure hafnium fraction and at least one waste fraction from said column.

2. The method of claim 1, in which said aqueous sulfate feedstock preparation of step (a) comprises:

(i) chlorinating crude zircon sand containing zirconium and hafnium in the presence of carbon and elevated temperatures to produce a crude zirconium tetrachloride and hafnium tetrachloride fraction;

(ii) dissolving the crude zirconium tetrachloride and hafnium tetrachloride fraction in a dilute sulfuric acid solution to produce a crude aqueous zirconium oxychloride and hafnium oxychloride solution;

(iii) precipitating said crude zirconium oxychloride and hafnium oxychloride solution in a concentrated sulfuric acid solution to produce a crude zirconium sulfate and hafnium sulfate fraction; and, (iv) dissolving said crude zirconium and hafnium sulfate fraction in a dilute sulfuric acid solution to produce said aqueous sulfate feedstock solution.

3. The method of claim 2, in which the dissolution step (ii) is performed at a temperature from about 0° C. to 5° C. in order to reduce cross-polymerization reactions between zirconium and hafnium.

4. The method of claim 3, in which the dilute sulfuric acid of the dissolution step (ii) is at a concentration of about 0.5 to 2M and is added slowly in order to reduce spattering during evolution of gaseous hydrochloric acid.

5. The method of claim 2, in which the precipitation step (iii) is performed at a temperature from about 5° C. to ambient temperature.

6. The method of claim 5, in which the concentrated sulfuric acid of precipitation step (iii) is at a concentration of about 6M or greater in order to precipitate said zirconium sulfate and hafnium sulfate fraction from solution.

7. The method of claim 2, in which the dilute sulfuric acid of dissolution step (iv) is at a concentration from about 2 to 4M.

8. The method of claim 7, in which the dilute sulfuric acid of dissolution step (iv) is at a concentration from about 2M.

9. The method of claim 1, in which the aqueous sulfate eluant of step (c) comprises sulfuric acid.

10. The method of claim 9, in which the aqueous sulfuric acid eluant is at a concentration from about 1 to 4M.

11. The method of claim 10, in which the aqueous sulfuric acid eluant is at a concentration from about 1 to 2M $H_2SO_4$ for the hafnium elution and about 3 to 4M $H_2SO_4$ for the zirconium elution.

12. The method of claim 1, in which the zirconium product fraction of collection step (d) comprises a product purity of less than 50 ppm hafnium in said zirconium product fraction in order to provide nuclear grade materials.

13. The method of claim 1, which further comprises:

(e) separately processing the zirconium fraction and hafnium fraction to produce nuclear grade zirconium and hafnium metal;

(f) volume reducing the waste fraction for disposal; and, (g) recycling the eluant for reuse in step (c).

14. The method of claim 1, which further comprises:

(e) separately chromatographically processing the zirconium fraction and hafnium fraction to produce isotopically enriched nuclear grade zirconium and hafnium.

15. The method of claim 1, which further comprises operating the column and aqueous sulfate feedstock solutions and aqueous sulfate eluant solutions at a temperature of from about 0° C. to 5° C.

16. A continuous method for separating and purifying zirconium from hafnium, which comprises:

(a) preparing an aqueous sulfate feedstock solution of zirconium and hafnium sulfate complexes;

(b) loading the aqueous sulfate feedstock solution onto an anionic exchange resin contained in a continuously operating ion exchange chromatographic column of a continuous annular chromatograph;

(c) feeding an aqueous sulfate eluant solution onto the anionic exchange resin to elute the aqueous sulfate feedstock solution along the ion exchange chromatographic column;

(d) rotating the continuous annular chromatograph during steps (b) and (c) while the aqueous sulfate feedstock solution and aqueous sulfate eluant solution flow through the anionic exchange resin;

(e) separately collecting a hafnium product fraction a zirconium product fraction and at least one waste fraction at separate collection locations on the continuous annular chromatograph;

(f) separately processing the hafnium fraction and the zirconium fraction to produce nuclear grade zirconium and hafnium; and, (g) recycling the aqueous sulfate eluant for reuse in step (c).

17. The method of claim 16, which further comprises:

(h) collecting a mixed zirconium and hafnium fraction, loading said mixed fraction onto the anionic exchange resin of step (b) and repeating steps (c) to (g).

18. The method of claim 17, which further comprises:

(i) separately collecting a product fraction at a collection location between the hafnium product fraction and the zirconium product fraction; and, (j) recycling said product fraction for reuse in step (b).

19. The method of claim 16, in which said elution step (c) is a gradient elution.

20. The method of claim 16, in which the method is performed in a single pass through the continuous annular chromatograph of step (b) .

* * * * *